United States Patent [19]
Juhasz et al.

[11] Patent Number: 6,146,375
[45] Date of Patent: Nov. 14, 2000

[54] DEVICE AND METHOD FOR INTERNAL SURFACE SCLEROSTOMY

[75] Inventors: Tibor Juhasz, Irvine, Calif.; Zachary S. Sacks, Ann Arbor, Mich.; Ronald M. Kurtz, Ann Arbor, Mich.; Gerard A. Mourou, Ann Arbor, Mich.

[73] Assignee: The University of Michigan, Ann Arbor, Mich.

[21] Appl. No.: 09/203,421

[22] Filed: Dec. 2, 1998

[51] Int. Cl.$^7$ ................................... A61B 18/18
[52] U.S. Cl. ..................................... 606/6; 606/5
[58] Field of Search ................. 606/3–5, 6, 10, 606/13, 17, 18; 128/898

[56] References Cited

U.S. PATENT DOCUMENTS

| | | |
|---|---|---|
| 3,769,963 | 11/1973 | Goldman et al. . |
| 4,391,275 | 7/1983 | Frankhauser et al. . |
| 4,580,559 | 4/1986 | L'Esperance . |
| 4,669,466 | 6/1987 | L'Esperance . |
| 4,887,592 | 12/1989 | Loertscher . |
| 4,907,586 | 3/1990 | Bille et al. . |
| 4,941,093 | 7/1990 | Marshall et al. . |
| 5,049,147 | 9/1991 | Danon . |
| 5,439,462 | 8/1995 | Bille et al. . |

OTHER PUBLICATIONS

Sacks Zachary, S. et al, Laser Spot Size as a Function of Tissue Depth and Laser Wavelength in Human Sclera; Proceedings of Applications of Ultrashort–Pulse Lasers in Medicine and Biology; SPIE vol. 3255; pp. 66–76; Jan., 1998; San Jose, California.

Sacks, Zachary S.; Femtosecond Transscleral Photodisruption for the Treatment of Glaucoma, pp. 2–37, 1998.

Sacks, Zachary S. et al, Spacially resolved transmission of highly focused beams through cornea and sclera between 1400 and 1800 nm; 5 pages.

Sacks, Zachary S. et al., Transscleral photodisruption for the treatment of glaucoma, 4 pages.

*Primary Examiner*—Linda C. M. Dvorak
*Assistant Examiner*—Ann Farah
*Attorney, Agent, or Firm*—Nydegger & Associates

[57] ABSTRACT

An ab interno method for transscleral photodisruption of tissue on the interior surface of the sclera includes selecting a wavelength for a laser beam. The selected wavelength may be either from a first range of wavelengths (0.4–1.4 $\mu$m) which is normally strongly scattered as it is transmitted through the sclera, or from a second range of longer wavelengths (1.5–2.5 $\mu$m) which is less scattered as it is transmitted through the sclera. If the first range of wavelengths is selected, a chemical agent may be applied to the sclera to make it effectively transparent, but this may not be necessary. In either case, the laser beam is focused directly through the sclera to a focal point on the interior surface of the sclera. Once focused, the laser beam is activated to photodisrupt scleral tissue at the focal point. The laser beam is then moved in a pattern and refocused at successive focal points to photodisrupt scleral tissue at each of the focal points. This continues until the desired volume of scleral tissue has be photodisrupted, and thereby removed, from the interior surface of the sclera. The use of ultrashort laser pulses (in the femtosecond or picosecond range) is advantageous in order to achieve high precision and avoid collateral tissue damage. Such collateral damage is known to cause unwanted healing effects which are known to result in surgical failure.

13 Claims, 3 Drawing Sheets

DEVICE AND METHOD FOR INTERNAL SURFACE SCLEROSTOMY

This invention was made with government support under contract No. STC PHY 8920108 awarded by the National Science Foundation. The government has certain rights in the invention.

FIELD OF THE INVENTION

The present invention pertains generally to methods and procedures for use in ophthalmic surgery. More particularly, the present invention pertains to the use of laser devices for photodisruption of tissue in the eye. The present invention is particularly, but not exclusively, useful for an ophthalmic surgical procedure involving transscleral photodisruption of tissue on the interior surface of the sclera or limbus for relief of glaucoma.

BACKGROUND OF THE INVENTION

Glaucoma is a disease of the eye which is generally characterized by increased intraocular pressure within the eyeball and a progressive loss of vision. Typically, the treatment of glaucoma relies on the creation of a drainage channel which allows for the outflow of aqueous fluid from the eye. Heretofore, this has been mostly accomplished mechanically using instruments which cut externally into the sclera and its overlying episclera and conjunctiva. As an alternative to mechanical instruments which cut into the sclera, experimental laser treatments indicate that laser systems show promise.

Laser methods for use in the treatment of medical diseases are limited by the ability of the laser light to reach the tissue that is to be treated. Stated differently, depending on where the tissue is located, the tissue that is to be treated needs to either be exposed, or be at least somewhat transparent to the surgical laser beam that is to be used, or lie under a transparent layer of tissue. It happens that the transparency of tissue is dependent on its physical properties which affect the absorption and scattering of light by the tissue. Some of the specific factors affecting the transmission of light through biological tissue are age, medical condition, surface quality, hydration, temperature, and fluid content. In the context of the present invention, absorption relates to the tissues capacity to remove energy from the radiation and convert it into another form of energy. On the other hand, scattering is a general term for the irregular reflection or dispersal of light waves. With this in mind, it will be appreciated that absorption and scattering interact, with different results. In the case of a focused beam, absorption alone determines the maximum amount of energy that may reach a focal point. On the other hand, scattering determines the smallest possible focusable spot size.

As is well known, and obvious, the cornea of the eye is transparent to visible light. The sclera and the limbus, however, are not normally transparent to visible light. The limbus is the transition between the cornea and sclera and from the point of view of this transition it can be regarded as sclera. Nevertheless, it is interesting to note that the tissues of both the sclera and the cornea have similar anatomical structures. The main difference between the two is that the collagen fibers of the cornea have different widths and different separation or spacing than do the collagen fibers of the sclera. The consequence of this is that, unlike the cornea, the sclera effectively scatters light.

Heretofore, laser surgery on the sclera has been primarily accomplished using ab externo procedures which ablate tissue from the external surface of the sclera. These ab externo procedures have been done either by directing the laser light through the conjunctiva, or directly via a probe that is introduced under the conjunctiva. Ab externo procedures, however, can adversely disrupt the overlying conjunctiva and episclera. The only alternative, till now, has been ab interno procedures which are employed to ablate tissue from the internal surface of the sclera. Presently used Ab inferno procedures are accomplished either by directing the light through the cornea with a contact lens or directly via a probe that is introduced into the anterior chamber of the eye. Such procedures, however, are labor intensive and not reliably efficacious.

In a radically different approach to this problem, the present invention recognizes that new ab interno procedures are possible by directly focusing light through the sclera or the limbus of the cornea. To do this, the new ab inferno procedures of the present invention effectively avoid the severe scattering of light that is caused by the sclera under normal conditions. The first method is to select and use wavelengths for the laser beams which are effectively transparent to the sclera. The second is to decrease the tissue index mismatch and thereby widen the bandwidth of sclera transparency to include light in the visible and near infrared range.

A third method may be used which effectively combines the above-mentioned first and second methods. For all methods of the present invention it is to be appreciated that ultrashort laser pulses are to be used (e.g. picosecond or femtosecond pulses) in order to make better incisions. This result is achieved because ultrashort laser pulses will have deterministic thresholds and will cause much less of the collateral damage which is believed to be responsible for undesired healing responses in surgical operations for glaucoma.

In light of the above, it is an object of the present invention to provide a method for ab inferno transscleral photodisruption of tissue which operates at wavelengths for which the sclera is effectively transparent. It is another object of the present invention to provide a method for ab inferno transscleral photodisruption of tissue which involves treating the sclera to make the sclera effectively transparent to the wavelengths of the laser beams. Still another object of the present invention is to provide a device for ab interno transscleral photodisruption of tissue. Yet another object of the present invention is to provide a method and device for the ab interno transscleral photodisruption of tissue which is relatively easy to manufacture and simple to use, as well as being comparatively cost effective.

SUMMARY OF THE PREFERRED EMBODIMENTS

An ab interno method for transscleral photodisruption of tissue on the interior surface of the sclera in accordance with the present invention includes the step of first selecting a wavelength, $\lambda$, for a laser beam. Specifically, the selection of the wavelength $\lambda$ can be made from one of two ranges. The first of these is for wavelengths, $\lambda$, which are known to be transmitted through the cornea. This range includes visible light and extends therefrom into the near infrared, i.e., wavelengths between approximately 0.4 $\mu$m and 1.4 $\mu$m. The second is for longer wavelengths for which transmission through the sclera and limbus may be increased due to decreased scattering. Wavelengths in this second range are found to be between approximately 1.5 $\mu$m and 2.5 $\mu$m. Importantly, the wavelength of the laser beam avoid the water absorption peaks at 1.45 $\mu$m, 1.9 $\mu$m, and 2.4 $\mu$m.

For procedures wherein any wavelength is used, it may be beneficial, but it may not be necessary, to apply an agent to the sclera or limbus to make them substantially transparent to the wavelength of the laser beam. This can be done by a topical application of the agent directly onto the sclera in the area where the procedure is to be performed. Further, for a more rapid response, the agent can be injected directly into the sclera. It is known that the drug HYPAQUE is effective for this purpose. Alternatively, OMNIPAQUE, may be used. Regardless, it is to be appreciated that the sclera is effectively transparent with less than forty percent (<40%) hydration, and with greater than eighty percent (>80%) hydration. Accordingly, any agent that dehydrates or over hydrates in these ranges can be used for the present invention. Further, it is to be appreciated that air can be used for drying the sclera to accomplish the purposes of the present invention.

With the sclera effectively transparent to the selected wavelength of the laser beam that is being used for the procedure, the laser beam is focused through the sclera and onto a focal point which is located on the interior surface of the sclera. Also, it is preferable for the laser beam to be a pulsed laser beam which has pulse durations in the picosecond, or femtosecond, range. The laser device is then activated to generate a pulsed laser beam to cause the photodisruption of scleral tissue at the focal point. As indicated above, for purposes of the present invention, the duration of pulses in the beam will be in the picosecond (ps) or femtosecond (fs) range. This may be important in order to avid collateral tissue damage, and thereby avoid unwanted healing responses. After photodisruption of the tissue at the focal point has been completed, the laser beam is refocused to another focal point. The tissue at the new focal point is then photodisrupted in a similar manner. This process is continued by moving the laser beam focal point in a pattern anywhere in the sclera until the desired amount of scleral tissue has been photodisrupted. Typical laser beam parameters for use with the methods of the present invention are established according the wavelength that is used.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
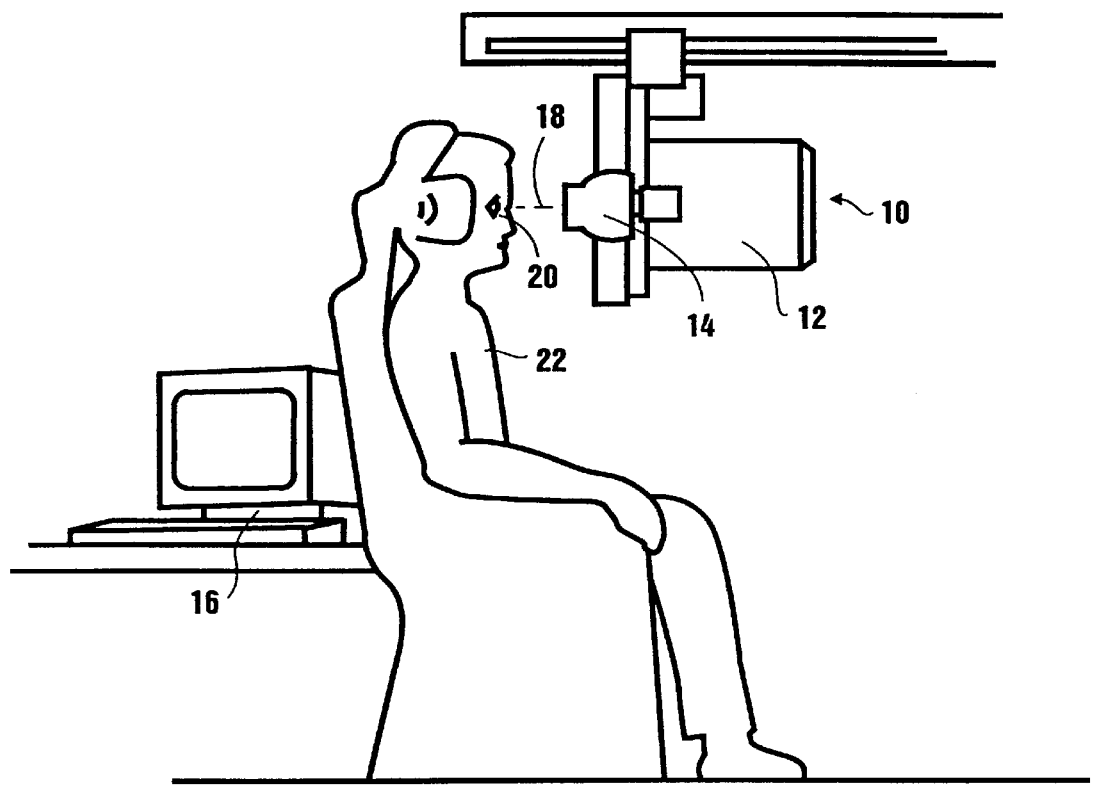
FIG. 1 is a perspective view of a patient positioned relative to a laser beam generator for purposes of the present invention.

Referring initially to FIG. 1 a laser device for use in ab inferno transscleral photodisruption of tissue on the interior surface of the sclera or limbus is shown and generally designated 10. In FIG. 1 it will be seen that the device 10 includes a laser beam generator 12 which has a focusing apparatus 14. Further, there is a computer 16 which is preprogrammed to operate both the laser beam generator 12 and the focusing apparatus 14 according to the desires of the operator. As intended for the present invention, operation of the device 10 results in the generation of a laser beam 18 which is directed toward the sclera 20 of a patient 22.

Figure 2:
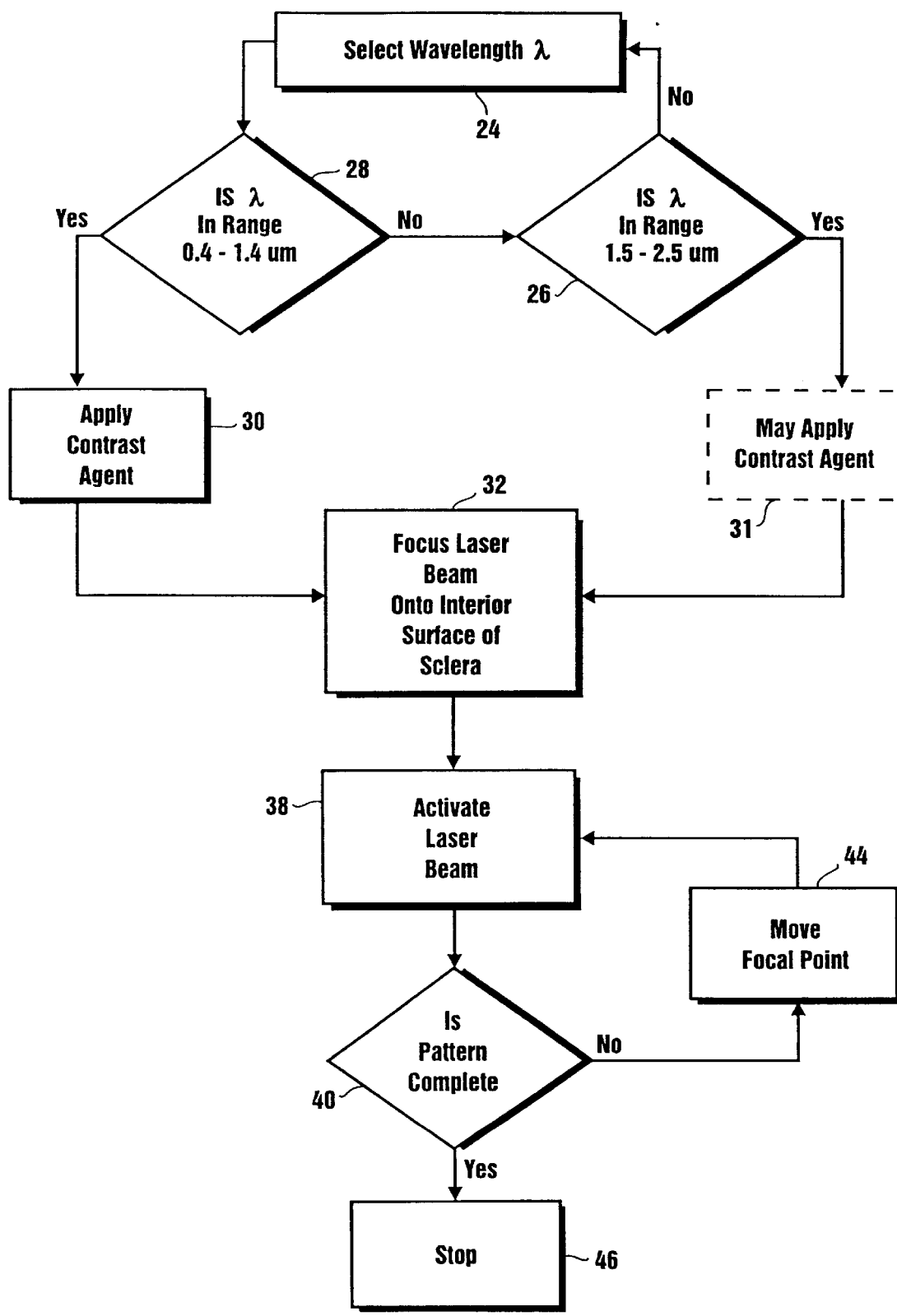
FIG. 2 is a flow chart showing the interrelationship of the steps involved in the methods of the present invention.
Figure 3:
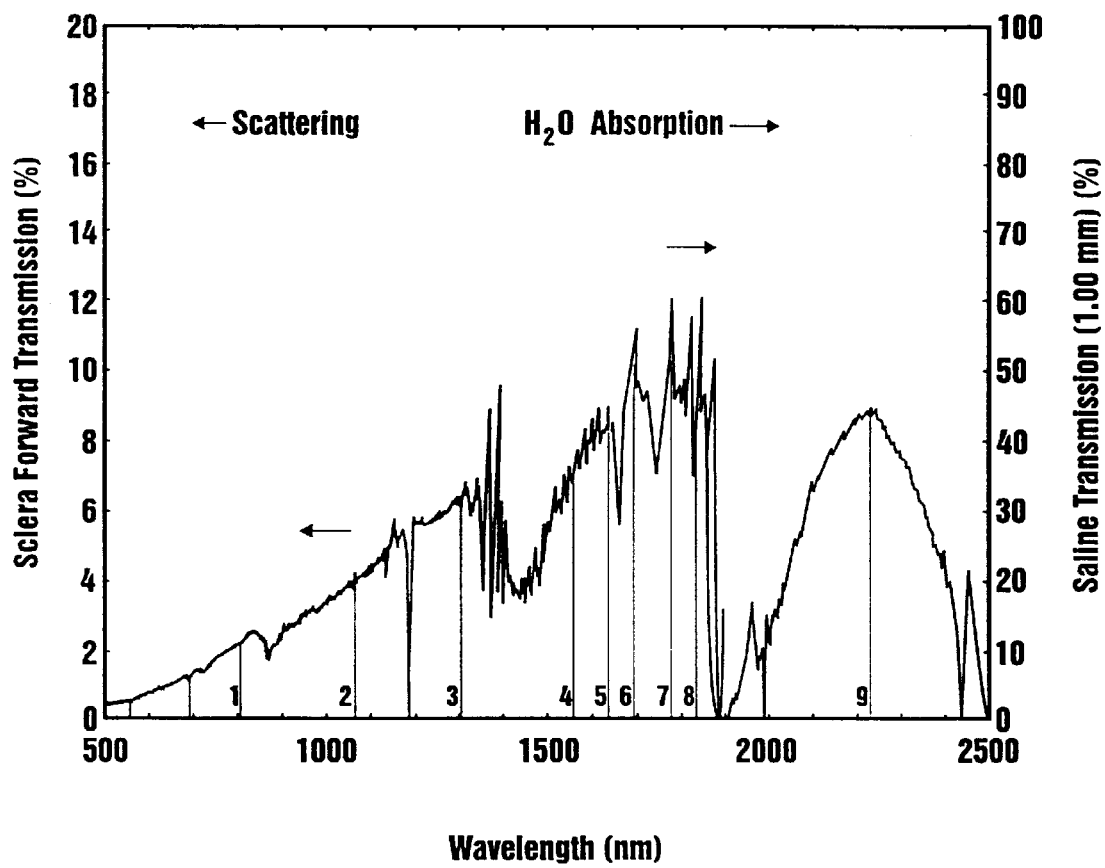
FIG. 3 is a graph, based on empirical data, which shows the transition of light through an untreated sclera as a function of wavelength, $\lambda$.

FIG. 2 shows a sequence of process steps for performing the methods of the present invention. As shown, the methods of the present invention begin with the selection of a wavelength $\lambda$ for the laser beam 18 (block 24). The selection of a wavelength, $\lambda$, is important for, as shown in FIG. 3, the untreated sclera will be semi-transparent to only certain wavelengths. As shown in FIG. 3, the maximum transmission of light through the sclera occurs at wavelengths, $\lambda$, around 1.7 $\mu$m. Interestingly, only about twelve percent of the incident light is transmitted through the sclera at this wavelength. Accordingly, as indicated below, a chemical agent may be helpful when the larger wavelengths are used.

Blocks 26 and 28, and the interaction of these blocks 26, 28 with block 24, indicate that the wavelength $\lambda$ is to be selected generally from a first range of wavelengths between 0.4 $\mu$m and 1.4 $\mu$m (0.4 $\mu$m<$\lambda$<1.4 $\mu$m), a second range of wavelengths between 1.5 $\mu$m and 2.5 $\mu$m (1.5 $\mu$m<$\lambda$<2.5 $\mu$m). These ranges, however, are only preferable and it is to be appreciated that other wavelengths can be used for the present invention. The first range of wavelengths includes visible light which experiences strong scattering by the sclera 20, while the second range of wavelengths include longer wavelengths that experience less scattering through the sclera 20. Block 30 of FIG. 2 also indicates that if a wavelength $\lambda$ is selected from the first range of wavelengths, a contrast agent or air should be applied to the sclera 20 in order to have the sclera 20 be transparent to the laser beam 18. Block 31 indicates that a contrast agent may be applied, but not necessarily, if a wavelength from the second range is chosen. Further, in either instance, it is to be appreciated that the contrast agent may be either topically applied or injected directly into the sclera 20 of patient 22.

Figure 4A:
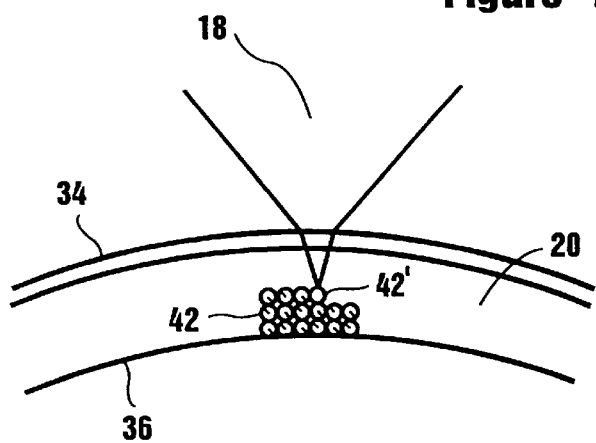
FIG. 4A is a cross sectional schematic view of the sclera of an eye during an operation employing the methods of the present invention.

After the wavelength $\lambda$ has been selected for laser beam 18 and a contrast agent applied if required (0.4 $\mu$m<$\lambda$<1.4 $\mu$m), the laser beam 18 is directed and focused (block 32) through both the conjunctiva 34 and the sclera 20. To do this of course, both the conjunctiva 34 and the sclera 20 are (or are treated to be) effectively transparent to the laser beam 18. As best appreciated with reference to FIG. 4A, the laser beam 18 is focused through the sclera 20 and onto the internal surface of the sclera 20. Specifically, the blocks 38 and 40 in FIG. 2 indicate that the laser beam 18 is activated and moved in a predetermined pattern to cause photodisruption of the scleral tissue at a sequence of ablation spots 42. Block 44 of FIG. 2 shows that, while the photodisruption of scleral tissue occurs instantaneously at only a single ablation spot 42', the focal point of laser beam 18 is moved through a series of focal points in the predetermined pattern to photodisrupt a volume of scleral tissue. Block 46 indicates the procedure is stopped when the pattern has been completed, and the desired volume of sclerol tissue has been ablated. As previously stated, the typical laser beam parameters which are used for the methods of the present invention are established according the wavelength that is used for laser beam 18. The use of ultrashort laser pulses (in the femtosecond or picosecond range), and the use of pulse energies close to the threshold, may be beneficial to achieve high precision and avoid collateral tissue damage, and therefore prevent unwanted heating. Pulse rates in the kHz range is preferable in order to achieve short procedure times.

Figure 4B:
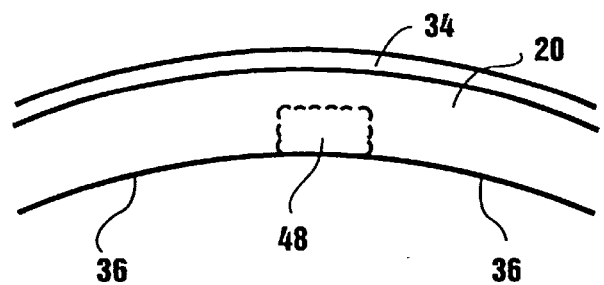
FIG. 4B is a cross sectional schematic view of the sclera of an eye after an operation employing the methods of the present invention.

The result of the methods of the present invention is that a channel, or spongy structure 48, shown in FIG. 4B, is created from the internal surface 36 and into the sclera 20 to relieve pressure in the eye. As stated above, the beneficial result of this procedure for the patient is that it serves as a cure for glaucoma.

While the particular surgical system design as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An ab interno method for transscleral photodisruption of tissue in the sclera or limbus which comprises the steps of:

generating a laser beam having a wavelength $\lambda$; and focusing said beam through the sclera to a point on the interior surface of the sclera for photodisruption of scieral tissue.

2. A method as recited in claim 1 wherein said wavelength $\lambda$ is in the range of approximately 0.4 $\mu$m to approximately 1.4 $\mu$m.

3. A method as recited in claim 2 further comprising the step of applying a chemical agent to the sclera to make the sclera substantially transparent to said wavelength $\lambda$ for said beam.

4. A method as recited in claim 3 wherein said applying step is accomplished by injecting said chemical agent into the sclera.

5. A method as recited in claim 2 wherein said generating step is accomplished using a laser source.

6. A method as recited in claim 1 wherein said wavelength $\lambda$ is in the range of approximately 1.5 $\mu$m to approximately 2.5 $\mu$m.

7. A method as recited in claim 1 further comprising the step of moving said focal point to a successive plurality of focal points in a predetermined pattern through the sclera to photodisrupt scleral tissue.

8. A method as recited in claim 7 wherein said moving step is accomplished by moving said focal point through a distance, and wherein said distance is approximately 10 $\mu$m.

9. A method for photodisruption of scleral tissue which comprises the steps of:

focusing a laser beam through the sclera of an eye to a focal point in the sclera, said laser beam having a wavelength $\lambda$, wherein said wavelength $\lambda$ is in the range of approximately 0.4 $\mu$m to approximately 1.4 $\mu$m;

generating a plurality of laser pulses to photodisrupt tissue at the focal point in the sclera; and moving said focal point to a successive plurality of focal points in a predetermined pattern through the sclera to photodisrupt scleral tissue.

10. A method as recited in claim 9 further comprising the step of applying a chemical agent to the sclera to make the sclera substantially transparent to said wavelength $\lambda$ for said beam.

11. A method as recited in claim 10 wherein said applying step is accomplished by injecting said chemical agent into the sclera.

12. A method as recited in claim 9 further comprising the step of applying air to the sclera to make the sclera substantially transparent to said wavelength $\lambda$ for said beam.

13. A method as recited in claim 9 wherein the duration of each said pulse in said laser beam is in a range of approximately 20 fs–300 ps.

* * * * *

UNITED STATES PATENT AND TRADEMARK OFFICE
CERTIFICATE OF CORRECTION

PATENT NO. : 6,146,375
DATED : November 14, 2000
INVENTOR(S) : Juhasz et al.

It is certified that error appears in the above-identified patent and that said Letters Patent is hereby corrected as shown below:

Column 2, Line 7
DELETE
[ab intemo]
INSERT
--ab interno--

Column 2, Line 17
DELETE
[ab inferno]
INSERT
--ab interno--

Column 2, Line 37
DELETE
[ab inferno]
INSERT
--ab interno--

UNITED STATES PATENT AND TRADEMARK OFFICE
CERTIFICATE OF CORRECTION

PATENT NO. : 6,146,375
DATED : November 14, 2000
INVENTOR(S) : Juhasz et al.

It is certified that error appears in the above-identified patent and that said Letters Patent is hereby corrected as shown below:

Column 2, Line 41
DELETE
[inferno]
INSERT
--interno--

Signed and Sealed this

First Day of May, 2001

Attest:

NICHOLAS P. GODICI

*Attesting Officer*  *Acting Director of the United States Patent and Trademark Office*